(12) United States Patent
Deininger et al.

(10) Patent No.: US 12,053,635 B2
(45) Date of Patent: Aug. 6, 2024

(54) SEALS FOR LEAD PASSAGEWAYS OF IMPLANTABLE MEDICAL DEVICES

(71) Applicant: MEDTRONIC, INC., Minneapolis, MN (US)

(72) Inventors: Steven T. Deininger, Plymouth, MN (US); Jeffrey J. Clayton, Zimmerman, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 278 days.

(21) Appl. No.: 17/738,966

(22) Filed: May 6, 2022

(65) Prior Publication Data

US 2022/0362559 A1 Nov. 17, 2022

Related U.S. Application Data

(60) Provisional application No. 63/187,367, filed on May 11, 2021.

(51) Int. Cl.
*A61N 1/375* (2006.01)
*H01R 13/52* (2006.01)

(52) U.S. Cl.
CPC ......... *A61N 1/375* (2013.01); *H01R 13/5224* (2013.01); *H01R 2201/12* (2013.01)

(58) Field of Classification Search
None
See application file for complete search history.

(56) References Cited

U.S. PATENT DOCUMENTS

| | | | | |
|---|---|---|---|---|
| 7,736,191 B1 * | 6/2010 | Sochor | ................... | H01R 24/58 607/116 |
| 8,593,816 B2 * | 11/2013 | Iyer | ................... | H01R 43/20 361/728 |
| 2003/0163171 A1 * | 8/2003 | Kast | ................... | H01R 24/58 607/36 |
| 2010/0256695 A1 * | 10/2010 | Iyer | ................... | A61N 1/3754 607/2 |
| 2011/0184479 A1 * | 7/2011 | Kast | ................... | A61N 1/3752 607/2 |
| 2013/0070423 A1 * | 3/2013 | Iyer | ................... | A61N 1/3754 361/728 |
| 2017/0087358 A9 * | 3/2017 | Deininger | ................... | H05K 5/06 |
| 2019/0290920 A1 * | 9/2019 | Stevenson | ................... | H01R 4/58 |
| 2021/0178168 A1 * | 6/2021 | Janzig | ................... | A61N 1/3754 |
| 2021/0339029 A1 * | 11/2021 | Deininger | ................... | A61N 1/37514 |
| 2021/0348253 A1 * | 11/2021 | Frysz | ................... | H01G 4/236 |

* cited by examiner

*Primary Examiner* — Krystal Robinson
(74) *Attorney, Agent, or Firm* — WITHERS & KEYS, LLC

(57) ABSTRACT

Seals used within lead passageways of implantable medical devices for creating a seal to implantable medical leads inserted into the lead passageways include a body defining a lead passageway with an axial dimension. The body further defines a first circumferential protrusion extending radially a first distance into the lead passageway, and the body further defines a second circumferential protrusion separated from the first circumferential protrusion along the axial dimension. The second circumferential protrusion extends radially a second distance into the lead passageway, the second distance being less than the first distance. The body further defines a first circumferential depression immediately adjacent the first circumferential protrusion and between the first circumferential protrusion and the second circumferential protrusion.

18 Claims, 7 Drawing Sheets

SEALS FOR LEAD PASSAGEWAYS OF IMPLANTABLE MEDICAL DEVICES

RELATED APPLICATIONS

The present application claims priority to U.S. Provisional Application No. 63/187,367 filed on May 11, 2021, which is incorporated by reference herein.

TECHNICAL FIELD

Embodiments relate to seals that are placed in lead passageways of implantable medical devices.

BACKGROUND

A lead passageway such as a lead bore of implantable medical device includes one or more electrical connectors that make an electrical connection to corresponding electrical contacts on a proximal end of an implantable medical lead that is inserted into the lead bore. Conductors within the implantable medical lead carry electrical signals between the electrical contacts and electrodes located near a distal end of the lead. These electrical signals may be stimulation signals being delivered to tissue at the distal electrodes. These signals may additionally or alternatively be sensed physiological signals occurring at the distal electrode that are delivered to the sensing circuitry of the implantable medical device.

When carrying stimulation signals or sensed signals on the implantable medical lead, it is useful to electrically isolate the electrical contacts on the proximal end from each other as well as from the body tissue surrounding the implantable medical device. For instance, such isolation helps a signal intended for a given proximal contact and corresponding distal electrode to be delivered to that proximal contact and distal electrode while largely preventing any amount of the signal from leaking to the body or other proximal contact at the proximal end of the lead. Likewise, such isolation helps a sensed signal obtained at a given distal electrode to be delivered to the circuit path of the implantable device corresponding to the proximal contact paired to that distal electrode while largely preventing any amount of the signal from leaking to the body or other proximal contact at the proximal end of the lead. Likewise, other electrical signals present nearby the implantable medical device may be largely blocked from leaking into the lead bore.

Electrical isolation is provided by the presence of seals within the lead bore of the implantable medical device. These seals typically are present between adjacent electrical connectors within the lead bore and also at the lead bore entrance at the surface of the implantable medical device. These seals may generally provide circumferential protrusions with an open center that has a smaller diameter than the lead diameter so that contact is made at the open center with the lead body which results in compression of the seal against the lead body to provide a seal about the lead body.

While a seal is formed, movement of the lead body in radial directions may stretch the opening of the protrusions which may form a small gap that allows small amounts of body fluid to pass by the seal. This lead body movement may occur during implantation or during normal body movement by the patient. While the small amount of fluid may not always be a concern, for situations where the electrical signals of interest are already very small yet other nearby signals are large, such as when a relatively small neurological signal of the brain is being sensed while relatively large cardiac signals are present near the implantable medical device, a small amount of fluid ingress to the lead bore may cause enough signal leakage to be problematic.

SUMMARY

Embodiments address issues such as these and others by providing a seal for an implantable medical device that provides a radially extending protrusion that the lead contacts upon insertion which causes the radially extending portion to bend and create a cylindrical shape that engages the lead body. This creates a seal that allows lateral and off-axis movement of the lead while maintaining the seal against the lead body.

Embodiments provide a seal that includes a body defining a lead passageway with an axial dimension, the body further defining a first circumferential protrusion extending radially a first distance into the lead passageway, the body further defining a second circumferential protrusion separated from the first circumferential protrusion along the axial dimension, the second circumferential protrusion extending radially a second distance into the lead passageway, the second distance being less than the first distance, the body further defining a first circumferential depression immediately adjacent the first circumferential protrusion and between the first circumferential protrusion and the second circumferential protrusion.

Embodiments provide an implantable medical device that includes a housing defining an outer lead passageway providing an exterior opening and electrical contacts within the outer lead passageway. The implantable medical device further includes sensing circuitry electrically coupled to the electrical contacts and a seal present within the outer lead passageway between the electrical contacts and the exterior opening. The seal comprises a body defining a lead passageway with an axial dimension, the body further defining a first circumferential protrusion extending a first distance into the lead passageway, the body further defining a second circumferential protrusion separated from the first circumferential protrusion along the axial dimension, the second circumferential protrusion extending a second distance into the lead passageway, the second distance being less than the first distance, the body further defining a first circumferential depression immediately adjacent the first circumferential protrusion and between the first circumferential protrusion and the second circumferential protrusion.

Embodiments also provide a method of providing a sealed configuration of a proximal end of an implantable medical lead being installed in an implantable medical device. The method involves receiving the proximal end of the implantable medical device through an exterior opening and into an outer lead passageway of a housing of the implantable medical device. The method further involves passing the implantable medical lead through a seal present within the outer lead passageway. The seal includes a body defining a lead passageway with an axial dimension, the body further defining a first circumferential protrusion extending a first distance into the lead passageway, the body further defining a second circumferential protrusion separated from the first circumferential protrusion along the axial dimension, the second circumferential protrusion extending a second distance into the lead passageway, the second distance being less than the first distance, the body further defining a first circumferential depression immediately adjacent the first circumferential protrusion and between the first circumferential protrusion and the second circumferential protrusion. The implantable medical lead contacts the first circumferential protrusion and forces the first circumferential protrusion to bend toward and contact the second circumferential protrusion so that the first circumferential protrusion creates a sealed engagement with the implantable medical lead.

DETAILED DESCRIPTION

Embodiments include seals that create a sealed configuration by providing a radially extending protrusion that contacts a lead body of an implantable medical lead being inserted into an implantable medical device. The lead body forces the radial protrusion to bend which then creates a cylindrical engagement of the seal to the lead body. This allows the lead body to move radially as well as in off-axis manners while the seal remains in contact with the lead body to preserve the sealing relationship.

Figure 1:
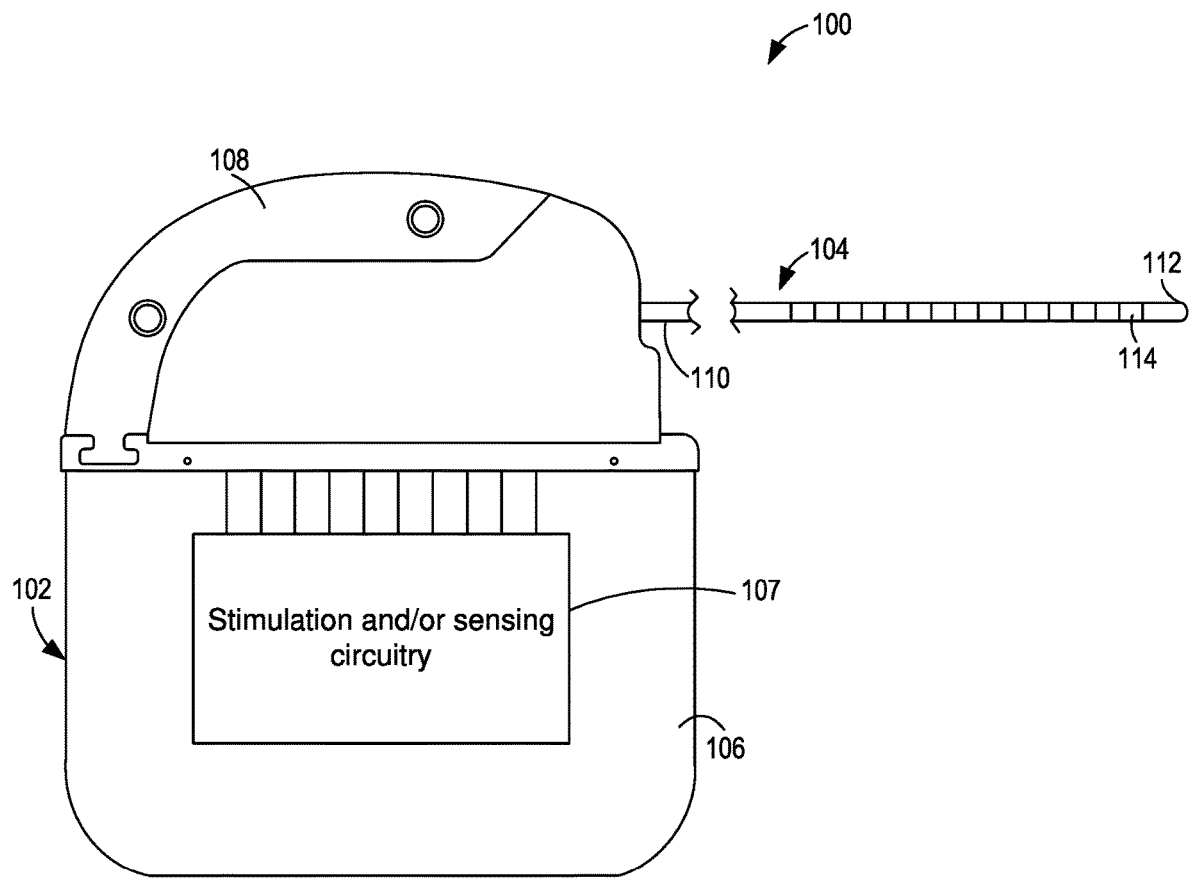
FIG. 1 shows a front view of an example of an implantable medical system that includes an embodiment of a seal.

FIG. 1 shows an example of an implantable medical system 100 that includes an implantable medical device 102 and an implantable medical lead 104. The implantable medical system 100 may be of any type such as a neuromodulation stimulation and/or sensing system, a cardiac stimulation and/or sensing system, and the like. The implantable medical lead 104 includes a proximal end 110 that is installed into a lead passageway of a header 108 of the implantable medical device 102. The header 108 is a housing for electrical contacts and is installed on a separately sealed housing 106 of the implantable medical device 102 that includes stimulation and/or sensing circuitry 107. As shown in subsequent figures and discussed below, the proximal end 110 has electrical connectors that are electrically coupled through the header 108 to the circuitry. Conductors within the lead 104 then carry the electrical signals between the circuitry of the housing 106 and electrodes 114 on a distal end 112 of the lead 104. The distal end 112 is positioned at the target stimulation and/or sensing site within the body.

Figure 2:
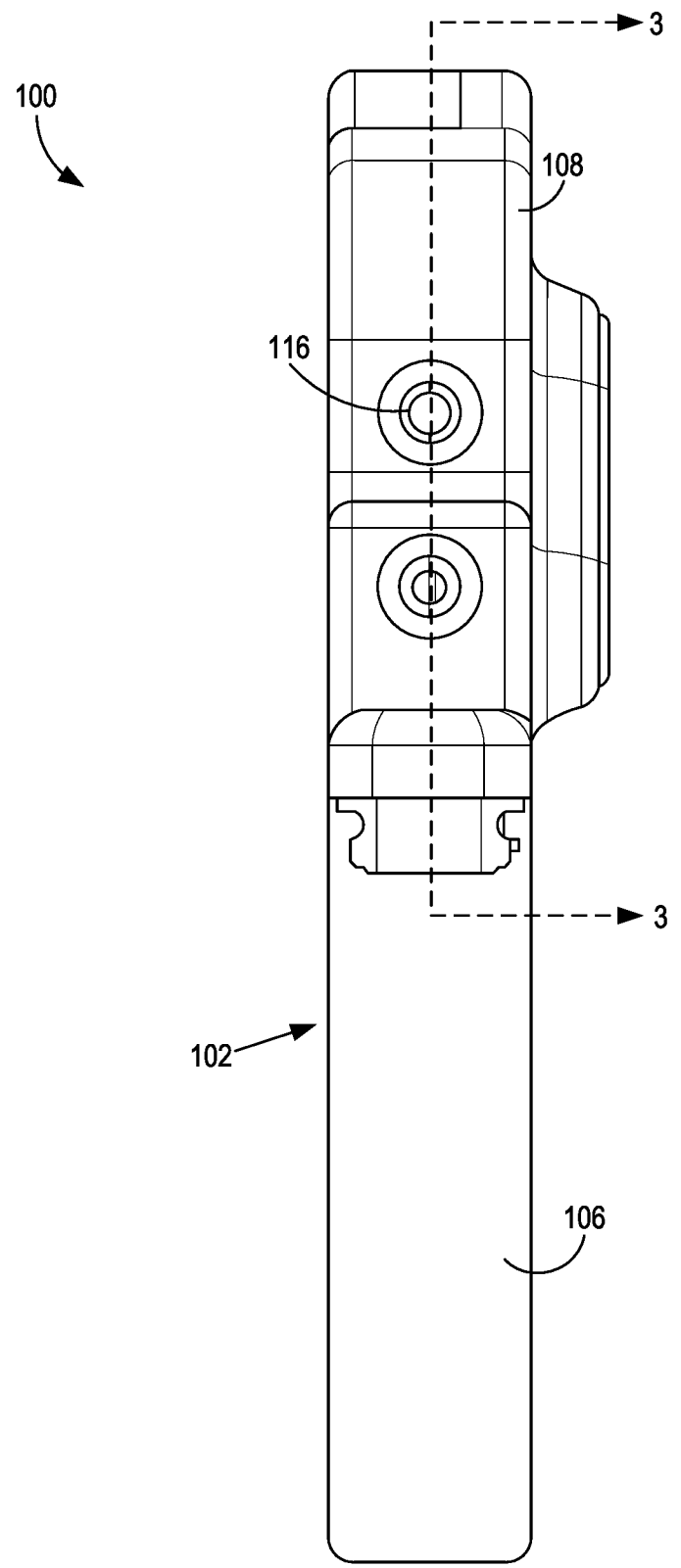
FIG. 2 shows a side view of an implantable medical device from the implantable medical system of FIG. 1.
Figure 3:
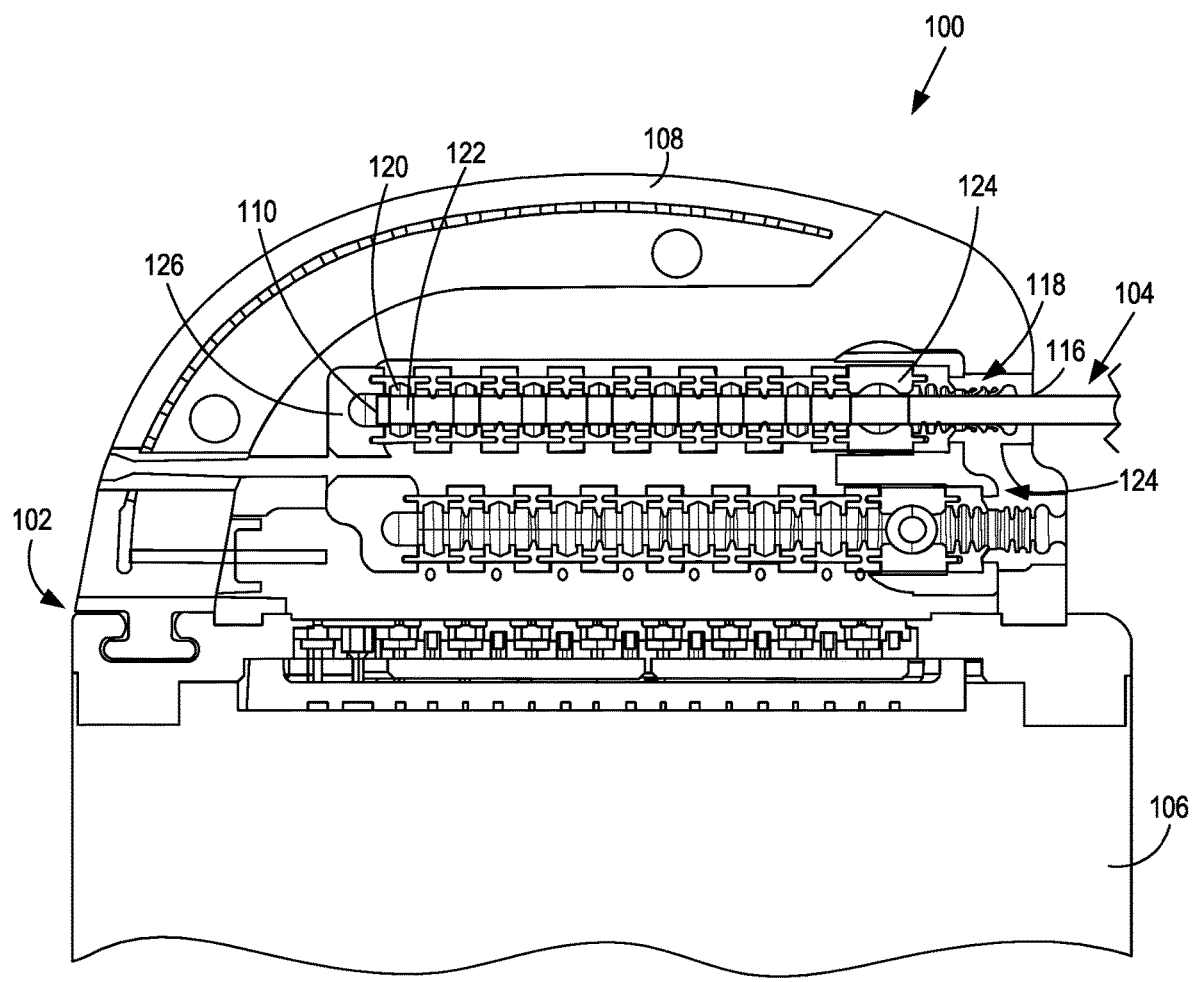
FIG. 3 shows a cross-sectional view along the axial dimension of an outer lead passageway of the implantable medical device from FIGS. 1 and 2.

FIG. 2 shows that the header 108 includes at least one exterior opening 116 that receives the proximal end 110 of the lead 104 while FIG. 3 shows the cross-sectional view 3-3 as indicated in FIG. 2. As shown in FIG. 3, the implantable medical device 102 includes an outer lead passageway 126 extending through the header 108 to the opening 116. An insulative filler material body 118 such as silicone has filled the outer lead passageway 126 in this example to provide mounting spaces for electrical contacts 120 and a set screw block 124. Examples of other filler materials that may be used for the filler material body 118 rather than silicone include polyurethane.

Figure 4:
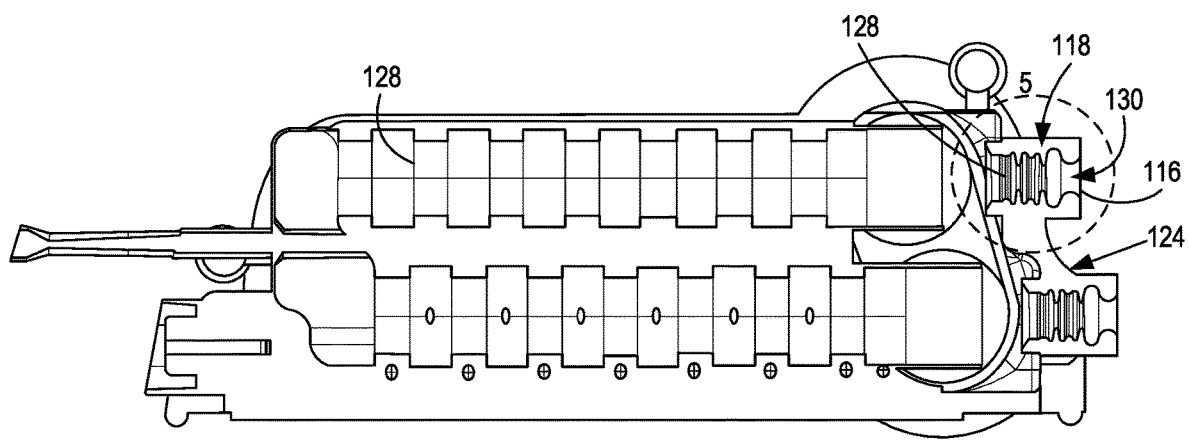
FIG. 4 shows a cross-sectional view of a non-conductive body that is present within the implantable medical device of FIG. 3 and that provides the embodiment of the seal.

FIG. 4 provides a cross-sectional view of the filler material 118 in isolation to demonstrate that a lead passageway 128 having an axial dimension extending through the header 108 as shown is present. The lead passageway 128 and axial dimension extends through the area where the spaces are created for the electrical contacts 120 and the set screw block 124 and extends forward to a seal 130 that includes a seal body 118 that provides the opening 116. The lead passageway 128 continues through the seal body 118 to the opening 116. As can be seen in FIG. 3, the implantable medical lead has passed through the seal body 118 in the lead passageway 128 until reaching a fully inserted position. A most proximal electrical connector 122 of the lead 104 has made physical and electrical contact with a most proximal electrical contact 120.

Figure 5:
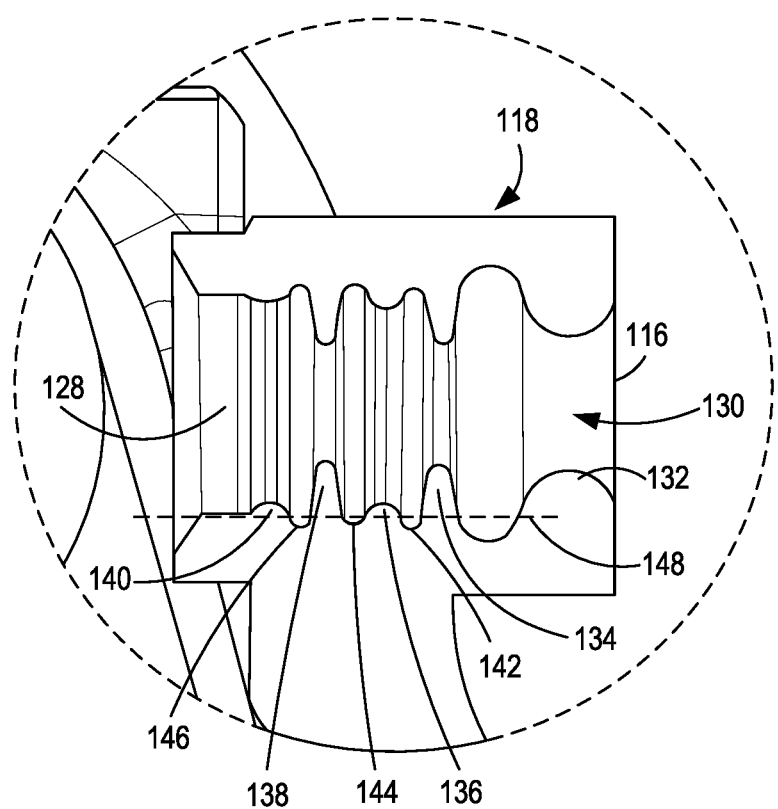
FIG. 5 shows a cross-sectional view of the embodiment of the seal.
Figure 6:
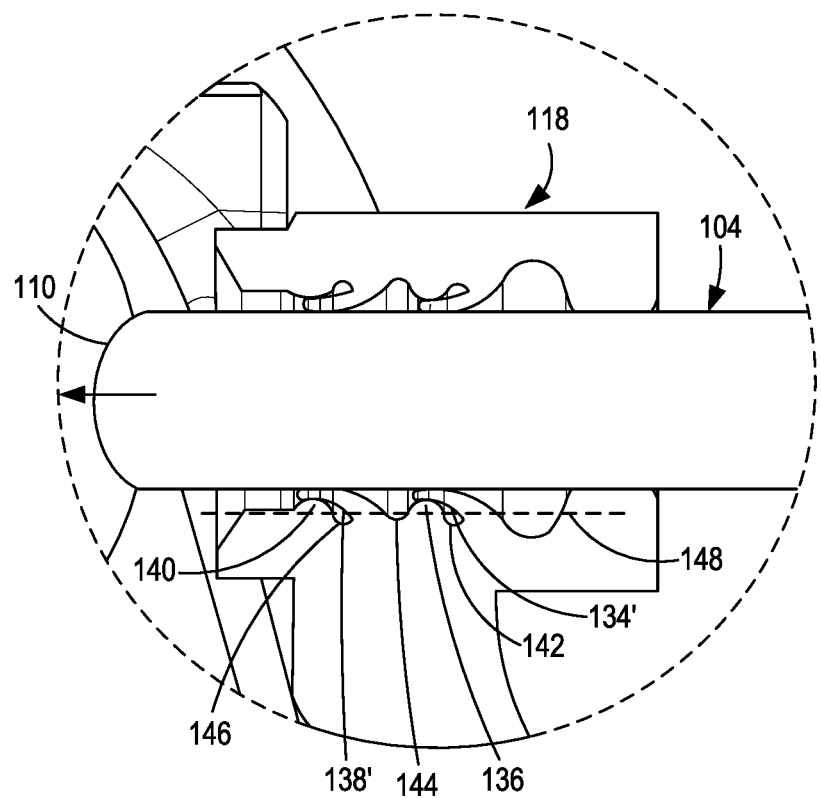
FIG. 6 shows a cross-sectional view of the embodiment of the seal as the implantable medical lead is being installed.

Returning to FIG. 4, it can be seen that the seal 130 including the seal body 118 is indicated as being shown in a magnified view in FIG. 5 to better illustrate the individual features of the seal 130. FIG. 5 shows the cross-sectional view of the seal 130 prior to the insertion of the lead 104. Here, it can be seen by reference line 148 that the lead passageway 128 passing through the seal body 118 has a given baseline that defines a point of measurement for the diameter of the lead passageway 128 of the seal body 118 relative to the diameter of the lead 104 that will pass through the lead passageway 128. In this example, the baseline of the lead passageway 128 through the seal body 118 as shown as measured from the reference line 148 is slightly larger than the diameter of the lead 104. This is shown in FIG. 6, which is discussed in more detail below.

Returning to FIG. 5, the seal body 118 includes at least one radially extending protrusion and at least one depression adjacent the at least one radially extending protrusion relative to the reference line 148. The at least one radially extending protrusion is present around the circumference of the inner surface of the seal body 118 and thus provides an opening with a diameter determined by the height of the protrusion relative to the reference line 148. The lead 104 then passes through the opening, albeit as an interference fit as discussed in more detail below in relation to FIG. 6.

In this particular example in FIG. 5, there are two longer radially extending protrusions 134, 138 that provide the interference fit with the lead 104 and two shorter radially extending protrusions 136, 140 that provide an opening with a diameter larger than the diameter of the lead 104 so that no interference occurs. The longer radially extending protrusions 134, 138 extend a first distance while the shorter radially extending protrusions 136, 140 extend a second distance where the first distance is greater than the second distance. The shorter radially extending protrusions are separated from the longer radially extending protrusions along the axial dimension of the lead passageway 128. Each of the radially extending protrusions 134, 136, 138, and 140 have a peak and a base and in this example, each narrows from the base to the peak as shown in FIG. 5.

Also, in this example of FIG. 5 there are three circumferential depressions 142, 144, and 146 where a first depression 146 and a second depression 144 are on each side of the first radially extending protrusion 138. The first depression 146 is between the first longer radially extending protrusion 138 and the first shorter radially extending protrusion 140. The second depression 144 is between the first longer radially extending protrusion 138 and the second shorter radially extending protrusion 136. A third depression 142 is located between the second shorter radially extending protrusion 136 and the second longer radially extending protrusion 134. A compression protrusion 132 is also included in the seal body 118 in this example at the opening 116 which provides a conventional compression fit against the lead 104. This compression fit by the compression protrusion 132 may still be subject to leakage for radial or off-axis movements of the lead 104. However, the presence of the longer radially extending protrusions account for any leakage at the compression protrusion 132 of the seal body 118.

The radially extending protrusions and adjacent depressions provide a sealing effect upon the lead being inserted as shown in FIG. 6. As discussed above, the longer radially extending protrusion(s) create an opening with a diameter smaller than the diameter of the lead 104 so that insertion of the lead 104 creates interference against the longer radially protrusion(s). As the lead 104 insertion continues into the lead passageway of the seal body 118, the at least one longer radially extending protrusion bends in a hinge-like manner, the movement being unobstructed due to the presence of the at least one adjacent depression. The result is that the relatively lengthy side, rather than just the relatively narrow tip, of the longer radially extending protrusion comes into contact with the lead 104 and creates a cylindrical sealing engagement to the lead 104. This cylindrical sealing engagement allows the lead 104 to move radially and/or off-axis while the sealing engagement between the longer radially extending protrusion and the lead 104 is maintained.

In the example of FIG. 6, the two longer radially extending protrusions 134, 138 are forced by the insertion of the lead 104 to hinge in the direction of lead insertion, taking advantage of the clearance provided by depressions 142 and 146. The fully hinged longer radially extending protrusions 134', 138' shown in the cross-sectional view of FIG. 6 each provide the cylindrical engagement to the lead 104. An additional feature of this example of FIG. 6 is the presence of the shorter radially extending protrusions 136, 140, and these shorter radially extending protrusions 136, 140 provide s stop for the longer radially extending protrusions 134, 138. As shown in FIG. 6, in the fully hinged position, the longer radially extending protrusions 134, 138 have come into contact with the shorter radially extending protrusions 136, 140, which provides a radial compression of the longer radially extending protrusions 134, 138 and the shorter radially extending protrusions 134, 138 to further enhance the sealing effect to the lead 104.

It will be appreciated that removal of the lead 104 from the lead passageway 128 results in the longer radially extending protrusions hinging in the reverse direction. Thus, the second depression 144 allows the first radially extending protrusion 138 to hinge toward the opening 116.

Figure 7:
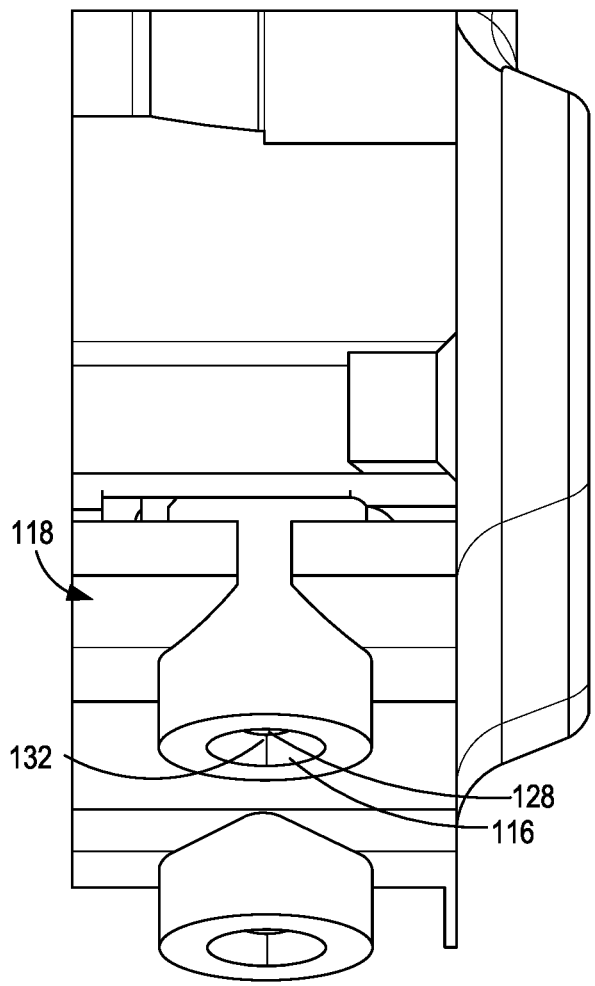
FIG. 7 shows a top perspective view of the embodiment of the seal.

To further illustrate the circumferential shape of the protrusions, it can be seen in FIG. 7 that the compression protrusion 132 at the opening 116 of the seal body 118 forms a circle to define the opening 116. It will be appreciated that the radially extending protrusions and depressions are also circumferential.

While specific examples of a seal 130 are disclosed above, it will be appreciated that there may be many variations. For instance, the number of longer radially extending protrusions may range from one to as many that will fit in the allotted space within the seal body 118. Likewise, it will be appreciated that the number of shorter radially protruding extensions and depressions may vary as well. Additionally, it will be appreciated that the location of the radially extending protrusions may vary. For instance, additional space may exist between the radially extending protrusions. Furthermore, other seal features may exist between the radially extending protrusions, such as a compression protrusion that does not hinge but is present between the radially extending protrusions with adequate spacing to avoid interfering with the hinge-like movement of the longer radially extending protrusions.

While embodiments have been particularly shown and described, it will be understood by those skilled in the art that various other changes in the form and details may be made therein without departing from the spirit and scope of the invention.

What is claimed is:

1. A seal for an implantable medical device, comprising:
a body defining a lead passageway with an axial dimension, the body further defining a first circumferential protrusion extending radially a first distance into the lead passageway, the body further defining a second circumferential protrusion separated from the first circumferential protrusion along the axial dimension, the second circumferential protrusion extending radially a second distance into the lead passageway, the second distance being less than the first distance, the body further defining a first circumferential depression immediately adjacent the first circumferential protrusion and between the first circumferential protrusion and the second circumferential protrusion.

2. The seal of claim 1, wherein the body further defines a third circumferential protrusion separated from the first circumferential protrusion along the axial dimension, the third circumferential protrusion extending radially the second distance into the lead passageway, the body further defining a second circumferential depression immediately adjacent the first circumferential protrusion opposite from the first circumferential depression and between the first circumferential protrusion and the third circumferential protrusion.

3. The seal of claim 2, wherein the body further defines a fourth circumferential protrusion extending radially the first distance into the lead passageway, the body further defining a third circumferential depression between the fourth circumferential protrusion and the third circumferential protrusion.

4. The seal of claim 1, wherein the body comprises silicone.

5. The seal of claim 1, wherein the first circumferential protrusion has a base and a peak and the first circumferential protrusion narrows from the base to the peak.

6. The seal of claim 1, wherein the second circumferential protrusion has a base and a peak and the base of the first circumferential protrusion is narrower than the base of the second circumferential protrusion.

7. An implantable medical device comprising:
a housing defining an outer lead passageway providing an exterior opening;
electrical contacts within the outer lead passageway;
sensing circuitry electrically coupled to the electrical contacts; and
a seal present within the outer lead passageway between the electrical contacts and the exterior opening, the seal comprising:
a body defining a lead passageway with an axial dimension, the body further defining a first circumferential protrusion extending a first distance into the lead passageway, the body further defining a second circumferential protrusion separated from the first circumferential protrusion along the axial dimension, the second circumferential protrusion extending a second distance into the lead passageway, the second distance being less than the first distance, the body further defining a first circumferential depression immediately adjacent the first circumferential protrusion and between the first circumferential protrusion and the second circumferential protrusion.

8. The implantable medical device of claim 7, wherein the body further defines a third circumferential protrusion separated from the first circumferential protrusion along the axial dimension, the third circumferential protrusion extending radially the second distance into the lead passageway, the body further defining a second circumferential depression immediately adjacent the first circumferential protrusion opposite from the first circumferential depression and between the first circumferential protrusion and the third circumferential protrusion.

9. The implantable medical device of claim 8, wherein the body further defines a fourth circumferential protrusion extending radially the first distance into the lead passageway, the body further defining a third circumferential depression between the fourth circumferential protrusion and the third circumferential protrusion.

10. The implantable medical device of claim 7, wherein the body comprises silicone.

11. The implantable medical device of claim 7, wherein the first circumferential protrusion has a base and a peak and the first circumferential protrusion narrows from the base to the peak.

12. The implantable medical device of claim 7, wherein the second circumferential protrusion has a base and a peak and the base of the first circumferential protrusion is narrower than the base of the second circumferential protrusion.

13. A method of providing a sealed configuration of a proximal end of an implantable medical lead being installed in an implantable medical device, comprising:
receiving the proximal end of the implantable medical device through an exterior opening and into an outer lead passageway of a housing of the implantable medical device; and
passing the implantable medical lead through a seal present within the outer lead passageway, the seal comprising:
a body defining a lead passageway with an axial dimension, the body further defining a first circumferential protrusion extending a first distance into the lead passageway, the body further defining a second circumferential protrusion separated from the first circumferential protrusion along the axial dimension, the second circumferential protrusion extending a second distance into the lead passageway, the second distance being less than the first distance, the body further defining a first circumferential depression immediately adjacent the first circumferential protrusion and between the first circumferential protrusion and the second circumferential protrusion,
such that the implantable medical lead contacts the first circumferential protrusion and forces the first circumferential protrusion to bend toward and contact the second circumferential protrusion so that the first circumferential protrusion creates a sealed engagement with the implantable medical lead.

14. The method of claim 13, wherein the body further defines a third circumferential protrusion separated from the first circumferential protrusion along the axial dimension, the third circumferential protrusion extending radially the second distance into the lead passageway, the body further defining a second circumferential depression immediately adjacent the first circumferential protrusion opposite from the first circumferential depression and between the first circumferential protrusion and the third circumferential protrusion.

15. The method of claim 14, wherein the body further defines a fourth circumferential protrusion extending radially the first distance into the lead passageway, the body further defining a third circumferential depression between the fourth circumferential protrusion and the third circumferential protrusion, such that the implantable medical lead contacts the fourth circumferential protrusion and forces the fourth circumferential protrusion to bend toward and contact the third circumferential protrusion so that the fourth circumferential protrusion creates a sealed engagement with the implantable medical lead.

16. The method of claim 13, wherein the body comprises silicone.

17. The method of claim 13, wherein the first circumferential protrusion has a base and a peak and the first circumferential protrusion narrows from the base to the peak.

18. The method of claim 13, wherein the second circumferential protrusion has a base and a peak and the base of the first circumferential protrusion is narrower than the base of the second circumferential protrusion.

* * * * *